(12) United States Patent
Orbay et al.

(10) Patent No.: US 7,604,657 B2
(45) Date of Patent: Oct. 20, 2009

(54) BONE FIXATION PLATE WITH COMPLEX SUTURE ANCHOR LOCATIONS

(75) Inventors: Jorge L. Orbay, Coral Gables, FL (US); Cesare Cavallazzi, Miramar, FL (US); Javier E. Castaneda, Miami, FL (US)

(73) Assignee: DePuy Products, Inc., Warsaw, IN (US)

( * ) Notice: Subject to any disclaimer, the term of this patent is extended or adjusted under 35 U.S.C. 154(b) by 275 days.

(21) Appl. No.: 11/466,905

(22) Filed: Aug. 24, 2006

(65) Prior Publication Data

US 2007/0093835 A1 Apr. 26, 2007

Related U.S. Application Data

(60) Provisional application No. 60/718,356, filed on Sep. 19, 2005.

(51) Int. Cl.
*A61B 17/80* (2006.01)
(52) U.S. Cl. ...................................... 606/280
(58) Field of Classification Search .................. 606/69, 606/280, 286, 291
See application file for complete search history.

(56) References Cited

U.S. PATENT DOCUMENTS

| | | | |
|---|---|---|---|
| 4,988,351 A * | 1/1991 | Paulos et al. ................. | 606/232 |
| 5,312,438 A | 5/1994 | Johnson | |
| 5,324,291 A | 6/1994 | Ries et al. | |
| 5,549,610 A | 8/1996 | Russell et al. | |
| 5,558,674 A | 9/1996 | Heggeness et al. | |
| 5,741,259 A | 4/1998 | Chan | |
| 6,344,042 B1 * | 2/2002 | Curtis et al. ................. | 606/298 |
| 6,468,278 B1 | 10/2002 | Muckter | |
| 6,623,486 B1 | 9/2003 | Weaver et al. | |
| 2003/0040748 A1 * | 2/2003 | Aikins et al. .................. | 606/70 |
| 2003/0083661 A1 * | 5/2003 | Orbay et al. .................. | 606/69 |
| 2004/0230196 A1 * | 11/2004 | Martello ...................... | 606/73 |
| 2005/0049593 A1 * | 3/2005 | Duong et al. ................. | 606/69 |
| 2005/0182405 A1 * | 8/2005 | Orbay et al. .................. | 606/69 |
| 2006/0189987 A1 * | 8/2006 | Orbay et al. .................. | 606/62 |

FOREIGN PATENT DOCUMENTS

| | | |
|---|---|---|
| EP | 0955013 A | 11/1999 |
| EP | 1464295 A2 | 10/2004 |

* cited by examiner

*Primary Examiner*—Eduardo C Robert
*Assistant Examiner*—Julianna N Harvey
(74) *Attorney, Agent, or Firm*—Gordon & Jacobson, PC

(57) ABSTRACT

A fracture fixation system includes a plate having a first suture anchor location having an opening at the upper surface of the plate, an opening at the proximal end of the plate, and an opening at the anterior side of the plate and defines first and second suture pathways which cross within the plate. The first and second suture pathways include a common opening. A second suture anchor location on the plate has an opening at the upper surface of the plate, an opening at the proximal end of the plate, and an opening at the posterior side of the plate which defines third and fourth suture pathways which cross within the plate. The third and fourth suture pathways also share a common opening. Thus, each suture anchor location is capable of providing a hold for suture from multiple approaches to secure tuberosities relative to the plate.

17 Claims, 3 Drawing Sheets

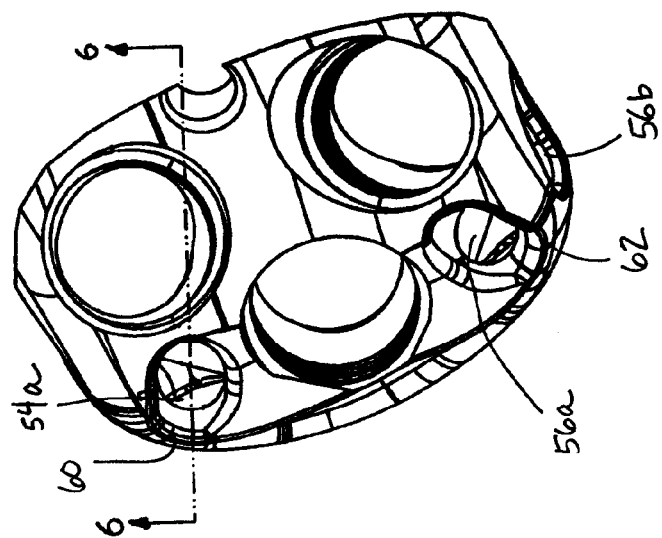
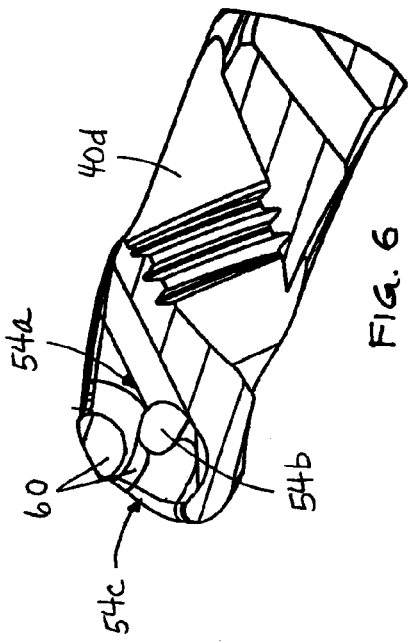
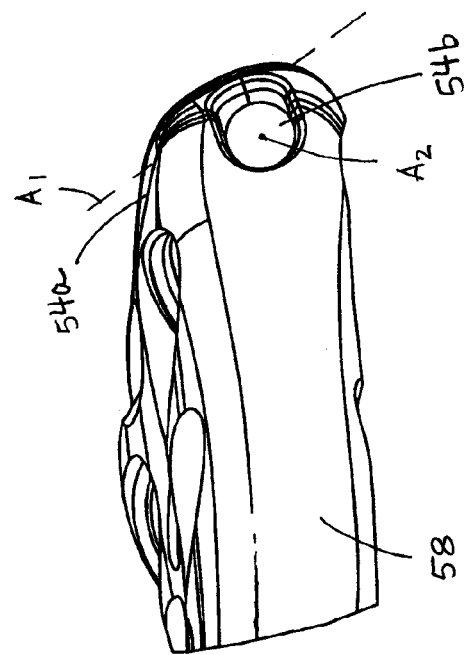

BONE FIXATION PLATE WITH COMPLEX SUTURE ANCHOR LOCATIONS

RELATED APPLICATIONS

This application claims the benefit of U.S. Ser. No. 60/718,356, filed Sep. 19, 2005, which is hereby incorporated by reference herein.

BACKGROUND OF THE INVENTION

1. Field of the Invention

This invention relates broadly to surgical devices. More particularly, this invention relates to orthopedic bone plates, particularly for fracture fixation, which include suture holes.

2. State of the Art

The proximal humerus comprises the upper portion of the humerus, i.e. upper arm of the human body, and forms a portion of the shoulder joint. Fractures of the proximal humerus typically result from traumatic injuries such as sporting accidents and can be more frequent with age due to bone loss. Fractures of the proximal humerus are treated by exposing the fracture site and reducing the bone fracture and then placing a plate onto the bone to fixate the fracture for healing in the reduced position. Reducing the fracture includes realigning and positioning the fractured portions of the bone to their original position or similar stable position. Fixating the fracture includes positioning a plate over the fractured portions and securing the plate onto the fractured bones and adjacent non-fractured bones with bone screws. Commonly, after a fracture there exist disassociated tuberosities at the proximal portion of the humerus. Tuberosities are pieces of bone with tendons attached. The bone is weak but the insertion points of the tendons are very strong. The accepted way to reattach the bone for healing is to use suture material to stitch into the insertion point of the tendon and pull down to anchor the bone with the suture.

Humeral plates often include suture holes at which suture material, e.g., braided cord or wire suture, can secure the tuberosities to the plate. The suture holes are generally circular holes extending transverse to the longitudinal axis of the plate. For example, the Philos™ plate by Synthes includes multiple suture holes displaced around the plate which extend between the bone contacting and lower plate surfaces. Because one opening of each suture hole is even with the bone contacting surface, access to or egress from the holes with a suture needle is impeded. In addition, U.S. Pat. No. 6,468,278 to Mückter describes a narrow humeral plate having only two suture holes which extend parallel to the bone contacting and upper surfaces. One hole is located at the proximal end of the plate and the other holes is located substantially distal. Given the orientation and location of the holes, the holes present limited approaches for tissue attachment. U.S. Pub. No. 20050182405 A1 to Orbay describes several humeral plates having individual suture holes arranged about the proximal end of the plate in a manner which permits easy access to the holes. However, the arrangement of holes causes the proximal head portion of the plate to be rather elongate. It is desirable to reduce the extension of the head portion as much as possible to prevent any impingement of the plate against the acromium.

SUMMARY OF THE INVENTION

A fracture fixation system includes a plate having head and shaft portions, wherein the head portion has two suture anchor locations occupying a relatively small space on the plate. A first suture anchor location has an opening at the upper surface of the plate, an opening at the proximal end of the plate, and an opening at the anterior side of the plate and defines first and second suture paths which cross within the plate. Moreover, the first and second suture paths include a common opening. A second suture anchor location has an opening at the upper surface of the plate, an opening at the proximal end of the plate, and an opening at the posterior side of the plate which defines third and fourth suture paths which cross within the plate. The third and fourth suture paths also share a common opening. Thus, each suture anchor location is capable of providing a hold for suture from multiple approaches to secure tuberosities relative to the plate.

Similar suture anchor holes may be provided on plates for fixation of other bones. Additional objects and advantages of the invention will become apparent to those skilled in the art upon reference to the detailed description taken in conjunction with the provided figures.

BRIEF DESCRIPTION OF THE DRAWINGS

FIG. 4 is an enlarged broken proximal end side elevation of the plate of FIG. 1;

FIG. 5 is an enlarged top perspective view of the proximal end of the plate of FIG. 1;

FIG. 6 is a section view across line 6-6 in FIG. 5; and

DETAILED DESCRIPTION OF THE PREFERRED EMBODIMENTS

Figure 1:
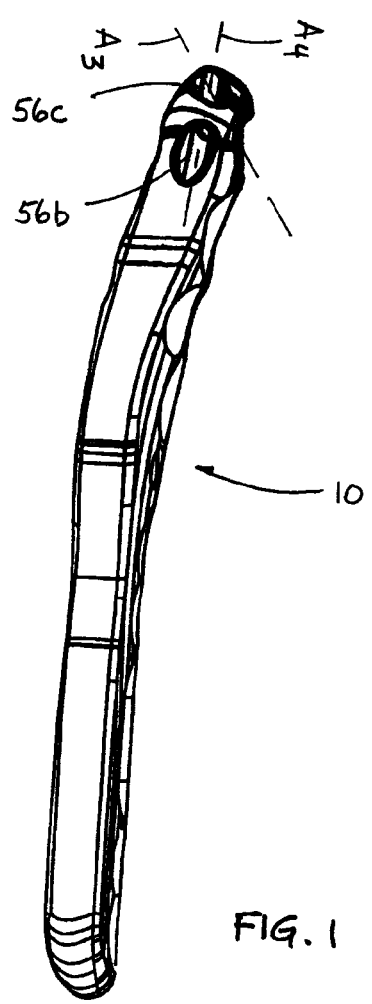
FIG. 1 is a side elevation view of a right arm proximal humeral fixation plate according to the invention.
Figure 2:
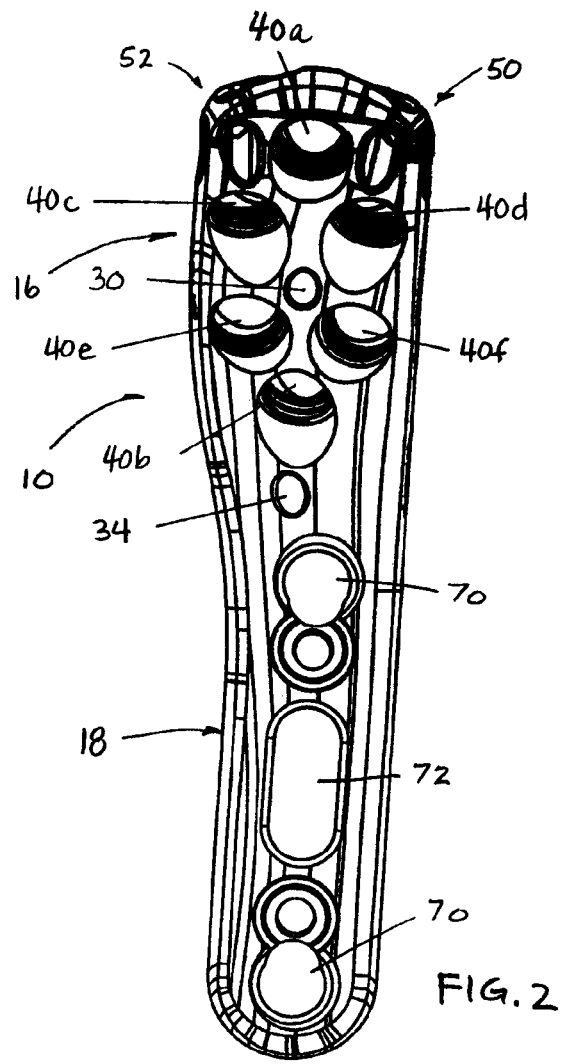
FIG. 2 is a plan view of the proximal humeral fixation plate of FIG. 1.
Figure 3:
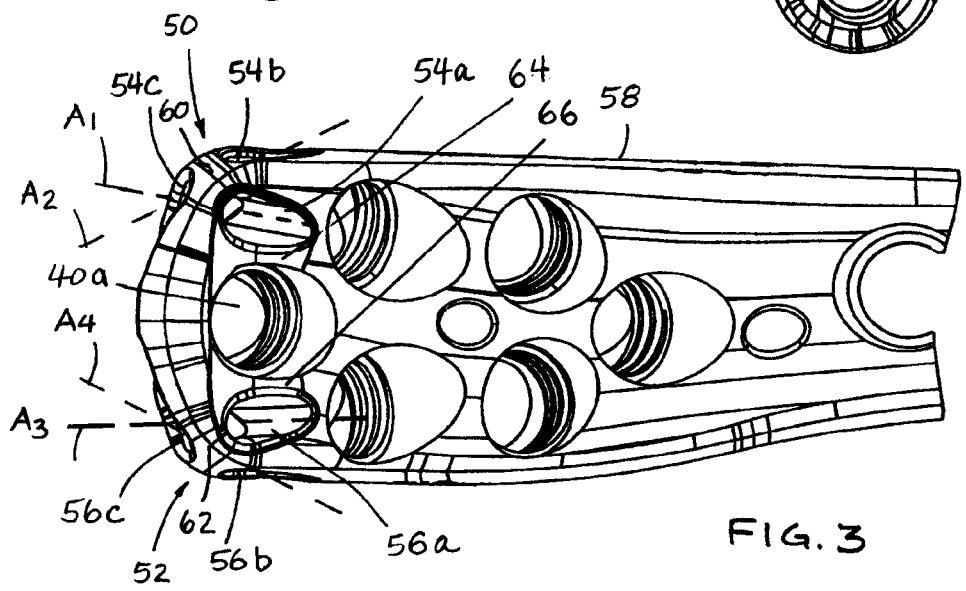
FIG. 3 is an enlarged broken proximal end plan view of the plate of FIG. 1.

Turning now to FIGS. 1 and 2, a humeral fracture fixation plate 10 includes a head portion 16 and shaft portion 18. The head portion 16 of plate includes a central alignment hole 30 for closely receiving a K-wire (not shown), and may also include other alignment holes such as distal alignment hole 34, to hold K-wires at a fixed angle to facilitate alignment of the plate 10 relative to the humerus, as described in detail in co-pending U.S. Ser. Nos. 11/040,732, filed Jan. 21, 2005, and 11/134,247, filed May 20, 2005.

The head portion 16 of the plate is provided with a plurality of threaded holes 40a-f. The threaded holes 40a-f have defined axes. More particularly, proximal and distal threaded holes 40a, 40b have axes which are in the same plane and converge toward a point substantially defined by central alignment hole 30. The axes of holes 40a, 40b are directed substantially perpendicular to the central portion of the articular surface of the humeral head. Axes through holes 40c, 40d are directed substantially perpendicular to the upper portion of the articular surface, but diverge to provide support. Axes through holes 40e, 40f are directed substantially perpendicular to the lower portion of the articular surface, and also diverge to provide support; however the divergence angle between the axes through 40e, 40f is smaller than between the axes of 40c, 40d. In addition, the axes through 40e, 40f are also angled relatively further away from the 'centerline' defined by alignment hole 30, placing the axes therethrough, and thus any pegs therethrough, close to the lowermost part of the articular surface, but orienting such pegs to provide support to prevent the humeral head from going into varus (i.e., in which the lower pegs could protrude through the cortex). Thus, there is an optimal asymmetry to the orientation of the axes (and pegs inserted therethrough).

Suture anchor locations 50, 52 are provided at the metaphyseal end of the head portion of the plate. For the humeral plate 10, locations 50, 52 are at the proximal anterior and posterior locations of the head portion 16 of the plate.

Referring to FIGS. 1 through 6, a first suture anchor location 50 includes an opening 54a at the upper surface of the plate, an opening 54b at the anterior side of the plate, and an opening 54c at the proximal end of the plate. A curved suture needle and suture can be passed between openings 54a and 54c along a pathway or path $A_1$. In an exemplar embodiment, Path $A_1$ has a diameter of approximately 0.08 inch. Path $A_1$ defines an axis angled in rotation approximately −9° relative to the straight anterior side 58 of the plate, and angled in inclination approximately 38°. Path $A_1$ (and all suture paths described herein) is of sufficient diameter and sufficiently short to permit a curved needle of an approximately 6.5 mm radius to be passed therethrough. It is understood that needles of other dimensions and radiuses will also pass through the defined paths, but that the 6.5 mm radiused needle referenced is a standard sized needle used in tendon repair at the proximal humerus. A curved suture needle can also be passed between openings 54b and 54c along a path $A_2$, which has a diameter of approximately 0.08 inch and defines an axis angled in rotation approximately 38° relative to anterior side 58 of the plate and angled in inclination approximately −3°. Even as paths $A_1$ and $A_2$ are obliquely angled relative to each other in two dimensions, the paths are in communication within the plate. Opening 54c serves as a common exit (or entrance) to both of openings 54a and 54b, such that within the plate paths $A_1$ and $A_2$ define a forked pathway relative to opening 54c. It is noted that corner 60 provides a boundary to both paths $A_1$ and $A_2$ which is shorter than the opposite wall of the respective paths. This facilitates insertion of the curved suture needle therethrough. As shown with respect to FIGS. 4 through 6, the paths $A_1$ and $A_2$ have a smaller diameter than holes 40a-f.

A second suture anchor location 52 has an opening 56a at the upper surface of the plate, an opening 56b at the posterior side of the plate, and an opening 56c at the proximal end of the plate. The curved suture needle and suture can be passed between openings 56a and 56c along a path $A_3$. Path $A_3$ has a diameter of approximately 0.08 inch and defines an axis angled in rotation approximately 4° relative to the anterior side 58 of the plate and angled in inclination approximately 39°. The curved suture needle can also be passed between openings 56b and 56c along a path $A_4$, which has a diameter of approximately 0.08 inch and defines an axis angled approximately −38° in rotation relative to anterior side 58 of the plate and angled approximately −7° in inclination. Even as paths $A_3$ and $A_4$ are obliquely angled relative to each other in two dimensions, the paths are in communication within the plate. Opening 56c serves as a common exit (or entrance) to both of openings 56a and 56b, such that within the plate paths $A_3$ and $A_4$ are forked relative to opening 56c. It is noted that corner 62 provides a boundary to both paths $A_3$ and $A_4$ which is shorter than the opposite wall of the respective paths. This facilitates insertion of the curved suture needle therethrough.

All of the openings 54a-c, 56a-c about which suture will be tied have rounded edges to prevent cutting or otherwise damaging the suture when the suture is under tension; e.g. the edges have a radius of 0.012-0.040 inch. Recesses 64, 66 are provided on the top of the plate between openings 54a and 56a on either side of peg hole 40a for receiving exposed suture materials in a low profile manner; i.e., recessed below the upper surface of the plate.

The shaft portion 18 of the plate includes a plurality of screw holes 70, 72. Screw holes (and associated screws) may be of the non-threaded locking-type (as per screw hole 70, may be non-locking (as per screw hole 72), or may be threaded locking (e.g., similar to the type hole shown for the peg holes).

Figure 7:
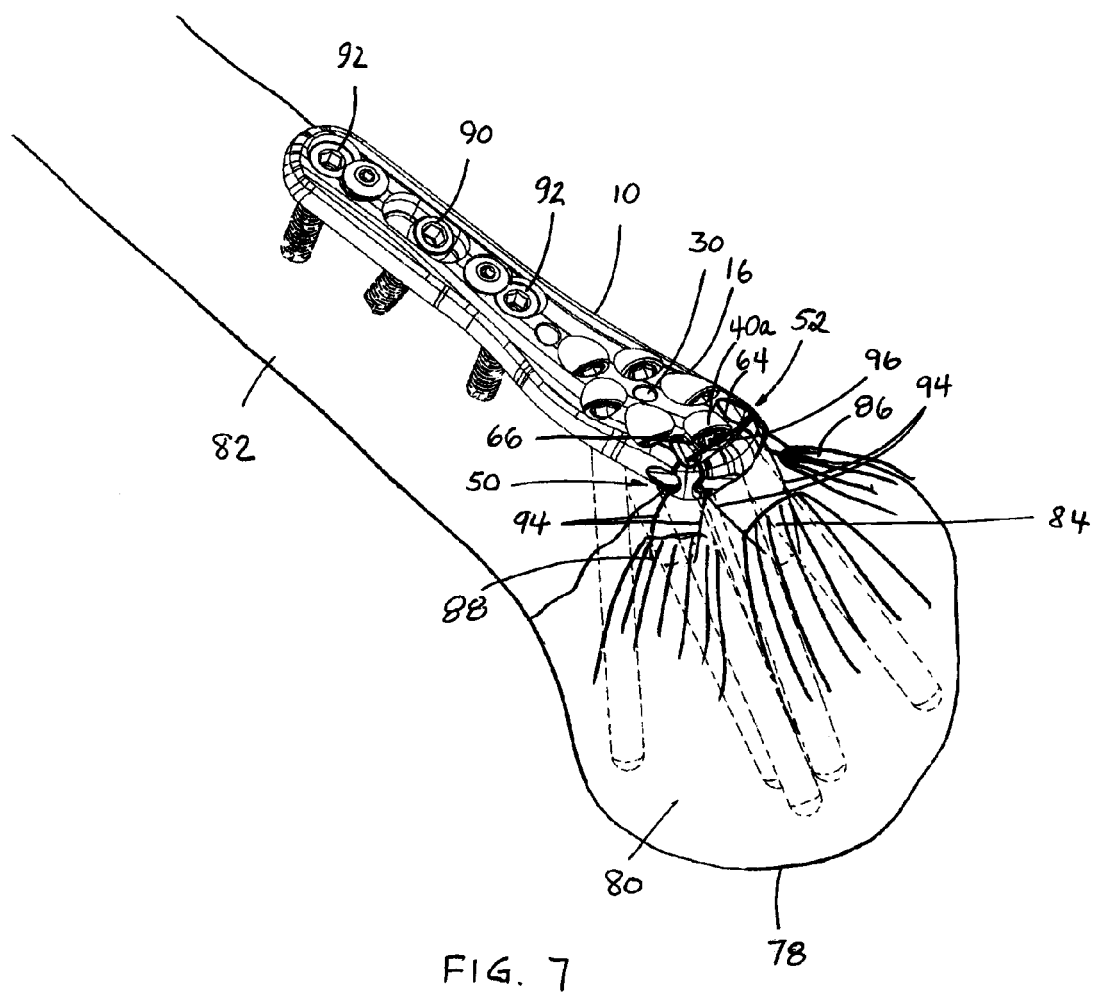
FIG. 7 is a perspective view showing a proximal humeral fixation system including the plate of FIG. 1, on the humerus.

Referring to FIG. 7, in accord with one method of using the system of the invention shown with respect to a left arm humerus and respective humeral plate, a delto-pectoral approach is developed to expose and debride the fracture. Traction and direct manipulation are then used to reduce the fracture. The anatomical relationship between the articular surface 78 of the humeral head 80 and the humeral shaft 82 are reestablished by restoring both angular alignment and rotation. Tuberosities (insertion points of supraspinitus 84, subscapularus 86 and infraspinitus 88 tendons) are examined for assurance that they can be reduced to their proper position.

The position of the plate 10 is then located, preferably immediately lateral to the intertubercle groove and approximately 2.5 cm below the insertion of the supraspinatus 84. The plate is secured to the distal fragment using a cortical screw 90 inserted through the non-locking oblong screw hole 72 or via a plate-holding clamp. The reduction is then locked using a K-wire (e.g., 2.0 mm) (not shown) inserted through the central fixed angle k-wire hole 30 on the head portion 16 of the plate 10 and into the proximal fragment(s) of the humeral head. The K-wire fixes the fracture and anticipates the final position of the pegs. The reduced fracture, plate location and K-wire are then evaluated using fluoroscopy (preferably both AP and axillary views) and readjusted as necessary.

Holes are then drilled through the peg holes 40a-f (FIG. 2) in alignment with their respective axes. The holes are preferably drilled manually after penetrating the cortex under power. The appropriate length and type of pegs (smooth shaft and/or threaded shaft) are selected and inserted using a driver and secured to the fixation plate. The distal end of the pegs should be 3-6 mm below the subchondral bone.

After peg placement, radiographic confirmation of correct fracture reduction and peg placement is preferably obtained. Then using a drill bit, holes are drilled for the remaining cortical screws that will be used to fix the distal shaft portion 18 of the plate 10 to the shaft 82 of the humerus. Either multidirectional screws, e.g., of type 90, or fixed angle screws 92 can be used.

Then, as necessary, tuberosities are reduced and fixed to the plate at the suture anchor locations 50, 52 using suture material 94. The arrangement of the suture locations 50, 52 and the suture paths $A_1$, $A_2$, $A_3$, $A_4$ (FIGS. 3-4) is such that stitching the three main tuberosities of the proximal humerus (i.e., bone fragments and the insertion points of the respective supraspinitus, subscapularus and infraspinitus tendons) is facilitated. In accord with a preferred method, using suture paths $A_1$ and $A_3$, a stitch can be made to tie down the supraspinitus tendon, with the suture material knotted so that the knot 96 rests over peg hole 40a and/or recesses 64, 66. Using suture path $A_2$, a stitch can be made to tie down the subscapularis tendon 86. Using suture path $A_4$, a stitch can be made to tie down the infraspinitus tendon 88.

Finally, the surgical site is closed using appropriate surgical technique.

In addition, it is recognized that each of the suture anchor locations may define three paths, with an additional path, e.g. between 54a and 54b, and between 56a and 56b. That is, at one suture anchor location the additional path is inclined and extends from the upper surface to the anterior side of the plate and at the other suture anchor location the additional path is inclined and extends from the upper surface to the posterior side of the plate.

In addition to machining, any of the paths may be manufactured or refined using diamond wire to remove plate material and smooth edges of the plate surrounding the paths.

There have been described and illustrated herein embodiments of a humeral fracture fixation system and methods of implanting the fracture system on the humerus. While a particular embodiment of the invention has been described, it is not intended that the invention be limited thereto, as it is intended that the invention be as broad in scope as the art will allow and that the specification be read likewise. Thus, the suture anchor system described can be applied to other orthopedic plates as well, particularly where such plates are intended to be used at or adjacent articulating surfaces where tuberosities may be present. It will therefore be appreciated by those skilled in the art that yet other modifications could be made to the provided invention without deviating from its scope as claimed.

What is claimed is:

1. A bone fixation plate for implanting on a bone, comprising:
    a bone plate having a bone contacting lower surface, an opposite upper surface such that when said lower surface is positioned on the bone, said upper surface is directed away from the bone, a side surface extending between said lower and upper surfaces along a length of said plate and an end surface extending between said lower and upper surfaces along a width of said plate, said length and width being transverse dimensions, and at least one suture anchor location, said suture anchor location including a first opening at said upper surface, a second opening at said side surface, and a third opening at said end surface, edges about said first, second and third openings are sufficiently radiused to prevent suture damage,
    said first and third openings defining a first suture pathway, said second and third openings defining a second suture pathway, wherein said first and second suture pathways cross within said plate.

2. A bone fixation plate according to claim 1, wherein:
    each of said pathways can receive a curved suture needle having a radius of curvature of approximately 6.5 mm.

3. A bone fixation plate according to claim 1, wherein:
    said first and second suture pathways have a diameter of approximately 0.08 inches.

4. A bone fixation plate according to claim 1, wherein:
    said first suture pathway includes a first axis, said second suture pathway includes a second axis, and said first and second axes are angled in two dimensions relative to each other.

5. A bone fixation plate according to claim 1, wherein:
    said plate includes two suture anchor locations.

6. A bone fixation plate according to claim 5, wherein:
    said plate includes a metaphyseal head portion and a shaft portion, and said upper surface, side surface and an end surface are located at said head portion.

7. A bone fixation plate according to claim 6, wherein:
    said plate is a proximal humeral plate including proximal and distal ends, and anterior and posterior sides, and said suture anchor locations are at said proximal anterior and proximal posterior locations on said head portion of said plate, such that said end surface is at said proximal end, and said side surface includes an anterior side surface for one of said suture anchor locations and a posterior side surface for another of said suture anchor locations.

8. A bone fixation plate according to claim 7, wherein:
    said head portion includes at least one threaded hole, and said shaft portion includes a plurality of screw holes.

9. A bone fixation plate according to claim 8, in conjunction with:
    a set of pegs each having a threaded head for engaging the at least one threaded hole in said head portion; and
    a set of cortical screws for insertion into said plurality of screw holes.

10. A bone fixation plate according to claim 5, wherein:
    said upper surface between the first openings of the two suture anchor locations is recessed for receiving suture material.

11. A bone fixation plate for implantation on a bone, said plate for use with suture material, comprising:
    a bone plate having a metaphyseal head portion at one end of said bone plate, said head portion provided with a first plurality of screw holes and a periphery about said first plurality of plurality of screw holes, said periphery including a bone contacting lower surface, an upper surface directed opposite said lower surface such that when said lower surface is positioned on the bone said upper surface is directed away from the bone, a side surface extending between said upper and lower surfaces along a lengthwise dimension of said plate, and an end surface extending between said upper and lower surfaces along a widthwise dimension of said plate, and defining first and second relatively oblique pathways for receiving the suture material, said first and second pathways each having a diameter smaller than said screw holes, said first and second pathways crossing within said plate, each of said first and second pathways being non-threaded and having edges sufficiently radiused to prevent damage to the suture material, wherein said first pathway is inclined relative to said upper surface and extends between said upper and end surfaces, and said second pathway extends between said side and end surfaces.

12. A bone fixation plate according to claim 11, wherein:
    said first and second pathways are sized and shaped to receive a curved suture needle having a radius of curvature of approximately 6.5 mm.

13. A bone fixation plate according to claim 11, wherein:
    said plate is a proximal humeral plate including proximal and distal portions, said proximal portion including said head portion and said distal portion including a shaft portion, said head portion including anterior and posterior portions,
    wherein said head portion includes two suture anchor locations located at proximal anterior and proximal posterior locations on said head portion, and
    said shaft portion including a second plurality of screw holes.

14. A bone fixation plate according to claim 13, wherein:
    each of said first plurality of screw holes is threaded.

15. A bone fixation plate for implanting on a bone, comprising:
    a proximal humeral bone plate having a shaft portion with a plurality of screw holes, said shaft portion defining a distal end of said plate, and a metaphyseal head portion having at least one threaded hole, said head portion defining a proximal end of said plate, a dimension of length of said plate defined between said proximal and distal ends said head portion including a bone contacting lower surface and an opposite upper surface such that when said lower surface is positioned on the humerus bone, said upper surface is directed away from the bone, said head portion also including an anterior side and a posterior side surface extending between said lower and upper surfaces along the length of said plate and an end surface extending between said lower and upper surfaces along a width of said plate, said length and width being transverse dimensions, said head portion also including a proximal anterior first suture anchor location and a proximal posterior second suture anchor location, said first suture anchor location including a first opening at said upper surface, a second opening at said anterior side surface, and a third opening at said end surface, said first and third openings of said first suture anchor location defining a first suture pathway of said first suture anchor location, said second and third openings of said first suture anchor location defining a second suture pathway of said first suture anchor location, wherein said first and second suture pathways of said first suture anchor location cross within said plate, and said second suture anchor location including a first opening at said upper surface, a second opening at said posterior side surface, and a third opening at said end surface, said first and third openings of said second suture anchor location defining a first suture pathway of said second suture anchor location, said second and third openings of said second suture anchor location defining a second suture pathway of said second suture anchor location, wherein said first and second suture pathways of said second suture anchor location cross within said plate.

16. A bone fixation plate according to claim 15, in conjunction with:
 a set of pegs each having a threaded head for engaging the at least one threaded hole in said head portion; and
 a set of cortical screws for insertion into said plurality of screw holes.

17. A bone fixation plate for implanting on a bone, comprising:
 a bone plate having a bone contacting lower surface, an opposite upper surface such that when said lower surface is positioned on the bone, said upper surface is directed away from the bone, first and second side surface extending between said lower and upper surfaces along a length of said plate and an end surface extending between said lower and upper surfaces along a width of said plate, said length and width being transverse dimensions, and first and second suture anchor locations, each said suture anchor location including a first opening at said upper surface, a second opening at one of said respective first and second side surface, and a third opening at said end surface, said first and third openings defining a first suture pathway, said second and third openings defining a second suture pathway, wherein said first and second suture pathways cross within said plate, and
 said upper surface of said plate between the respective first openings of the first and second suture anchor locations is recessed for receiving suture material.

* * * * *